US012800688B2

(12) United States Patent
Chitiboi et al.

(10) Patent No.: US 12,800,688 B2
(45) Date of Patent: Nov. 17, 2026

(54) AUTOMATIC INVERSION TIME SELECTION FOR FLOW-INDEPENDENT DARK BLOOD DELAYED ENHANCEMENT

(71) Applicant: Siemens Healthineers AG, Forchheim (DE)

(72) Inventors: Teodora Marina Chitiboi, Hamburg (DE); Andreea Bianca Popescu, Constanta (RO); Wolfgang Rehwald, Chapel Hill, NC (US)

(73) Assignee: Siemens Healthineers AG, Forchheim (DE)

( * ) Notice: Subject to any disclaimer, the term of this patent is extended or adjusted under 35 U.S.C. 154(b) by 426 days.

(21) Appl. No.: 18/660,238

(22) Filed: May 10, 2024

(65) Prior Publication Data

US 2025/0147136 A1 May 8, 2025

Related U.S. Application Data

(60) Provisional application No. 63/596,318, filed on Nov. 6, 2023.

(30) Foreign Application Priority Data

Nov. 6, 2023 (EP) .................................... 23465557

(51) Int. Cl.

| | |
|---|---|
| ***G01R 33/56*** | (2006.01) |
| ***A61B 5/00*** | (2006.01) |
| ***A61B 5/055*** | (2006.01) |
| ***G06T 7/11*** | (2017.01) |
| ***G06T 7/12*** | (2017.01) |

(52) U.S. Cl.

CPC ........ *G01R 33/5602* (2013.01); *A61B 5/0044* (2013.01); *A61B 5/055* (2013.01); *G01R 33/5607* (2013.01); *G01R 33/5608* (2013.01); *G06T 7/11* (2017.01); *G06T 7/12* (2017.01); *G06T 2207/10088* (2013.01); *G06T 2207/20081* (2013.01); *G06T 2207/20084* (2013.01); *G06T 2207/30048* (2013.01); *G06T 2207/30104* (2013.01)

(58) Field of Classification Search

None

See application file for complete search history.

(56) References Cited

U.S. PATENT DOCUMENTS

| | | | |
|---|---|---|---|
| 11,547,317 B2 | 1/2023 | Rehwald | |
| 2020/0237253 A1 * | 7/2020 | Rehwald .............. | A61B 5/0033 |

OTHER PUBLICATIONS

Chitiboi et al., "Deep Learning-based Strain Quantification from CINE Cardiac MRI", https://cds.ismrm.org/protected/20MProceedings/PDFfiles/0772.html, Publication Year: 2020 (Year: 2020).*

(Continued)

*Primary Examiner* — Chan S Park
*Assistant Examiner* — Promotto Tajrian Islam

(57) ABSTRACT

Systems and methods for automatically selecting an optimal inversion time for Flow-Independent Dark-blood Delayed Enhancement (FIDDLE). Deep learning is used to train a neural network to perform myocardium segmentation on REF images associated with FIDDLE images. A separate neural network is trained to find the intersection of the recovery curves of normal myocardium and blood pool. The intersection is used to determine the optimal inversion time.

19 Claims, 15 Drawing Sheets

(56) References Cited

OTHER PUBLICATIONS

Bhatt et al., "A Deep Learning Segmentation Pipeline for Cardiac T1 Mapping Using MRI Relaxation-based Synthetic Contrast Augmentation", DOI: 10.1148/ryai.210294, Publication Year: 2022 (Year: 2022).*
Guo et al., "Style Transfer-assisted Deep Learning Method for Kidney Segmentation at Multiphase MRI", DOI: 10.1148/ryai.230043, Publication Year: 2023 (Year: 2023).*
Kellman and Arai, "Cardiac imaging techniques for physicians: Late enhancement", DOI: 10.1002/jmri.2360, Publication Year: 2012 (Year: 2012).*
De Villedon de Naide et al., "Fully automated contrast selection of joint bright- and black-blood late gadolinium enhancement imaging for robust myocardial scar assessment", DOI: 10.1016/j.mri.2024.03.035, Publication Year: 2024 (Year: 2024).*
Popescu et al., "Automatic selection of optimal TI for flow-independent dark-blood delayed-enhancement MRI", DOI: 10.1002/mrm.30632, Publication Year: 2025 (Year: 2025).*
Bahrami, Naeim, et al. "Automated selection of myocardial inversion time with a convolutional neural network: Spatial temporal ensemble myocardium inversion network (STEMI-NET)." Magnetic resonance in medicine 81.5 (2019): 3283-3291.
Huang, Gao, et al. "Densely connected convolutional networks." Proceedings of the IEEE conference on computer vision and pattern recognition. 2017. 4700-4708.
Kim, Han W., et al. "Dark-blood delayed enhancement cardiac magnetic resonance of myocardial infarction." JACC: Cardiovascular Imaging 11.12 (2018): 1758-1769.
Olaf Ronneberger, Philipp Fischer, Thomas Brox, "U-Net: Convolutional Networks for Biomedical Image Segmentation", Medical Image Computing and Computer-Assisted Intervention (MICCAI), Springer, LNCS, vol. 9351: 234-241 (2015).
Yoon, S. et al: "A Deep-Learning-based Automated Myocardial Inversion Time Selection for Late Gadolinium Enhancement Imaging", SCMR 2021.
Zhu, J.-Y., Park, T., Isola, P. & Efros, A. A. (2017). Unpaired image-to-image translation using cycle-consistent adversarial networks. Proceedings of the IEEE International Conference on Computer Vision, Venice, Italy, pp. 2223-2232.
Yoon, Seung Su, et al. "Validation of a deep learning based automated myocardial inversiongadolinium enhancement imaging in a prospective study." Proceedings of the 29th scientificsociety for magnetic resonance in medicine, Online. 2021.

* cited by examiner

Prior Art

Prior Art

Conventional Bright-Blood LGE

FIDDLE (Dark-Blood LGE)

Prior Art

Prior Art

Prior Art

AUTOMATIC INVERSION TIME SELECTION FOR FLOW-INDEPENDENT DARK BLOOD DELAYED ENHANCEMENT

CROSS REFERENCE TO RELATED APPLICATIONS

This patent document claims the benefit of the filing date under 35 U.S.C. § 119(e) of U.S. Provisional Patent Application Ser. No. 63/596,318 filed on Nov. 6, 2023, which is hereby incorporated in its entirety by reference. This application also claims the benefit of EP 23465557.9 filed on Nov. 6, 2023, which is also hereby incorporated by reference in its entirety.

FIELD

This disclosure relates to medical imaging.

BACKGROUND

Late gadolinium enhancement (LGE) is a T1-weighted magnetic resonance imaging (MRI) acquisition technique commonly utilized for the assessment of acute and chronic myocardial injury. It is an important tool for the diagnosis and management of various cardiac conditions such as ischemic heart disease, infarction, and non-ischemic heart disease including myocarditis and multiple cardiomyopathies. LGE MRI relies on the administration of a T1-shortening contrast agent, typically a chelate of gadolinium, which selectively accumulates in the dead myocardial cells and areas of myocardial scar. In LGE images, this results in an increased signal intensity in these regions due to their shortened T1. T1-weighting is achieved by an inversion recovery (IR) pulse and a data acquisition (DA) timed to this pulse so that the recovery curve of normal, i.e., viable, healthy myocardium passes through the zero-magnetization point resulting in dark normal myocardium but bright infarcted, i.e., dead myocardium.

One issue with LGE is that it may be difficult to delineate diseased from normal tissue as diseased tissue adjacent to the cardiac cavity or vasculature often remains hidden since there is poor contrast between hyperenhanced tissue and bright blood-pool. One method for solving this issue uses a Flow-Independent Dark-blood DeLayed Enhancement technique (FIDDLE) that allows visualization of tissue contrast-enhancement while suppressing blood-pool signal. However, FIDDLE techniques also have issues in that the optimal inversion time (IT) is difficult to determine.

SUMMARY

By way of introduction, the preferred embodiments described below include methods, systems, instructions, and computer readable media for determining an optimal inversion time (TI) for Flow-Independent Dark-blood Delayed Enhancement (FIDDLE).

In a first aspect, a method for automatically calculating an optimal (or preferred) inversion time for flow independent dark-blood delayed enhancement (FIDDLE) is provided. The method includes: acquiring MR data of a patient, the MR data comprising a series of phase sensitive FIDDLE images, each having a different TI, and a series of phase reference images, each of which are associated with one phase sensitive FIDDLE image of the series of phase sensitive FIDDLE images; segmenting the series of phase sensitive FIDDLE images into a myocardial wall compartment and a blood pool compartment, using the series of phase reference images to derive the segmentation contours for the phase sensitive FIDDLE images; calculating, from the myocardial wall compartment, a signal of normal myocardium in each of the phase sensitive FIDDLE images; calculating, from the blood pool compartment, a signal of blood in each of the phase sensitive FIDDLE images; grouping each pair of the normal myocardium signal and its respective TI into a signal-versus-TI function that represents a recovery curve of normal myocardium, and grouping each pair of the blood signal and its respective TI into a signal versus-TI function that represents a recovery curve of blood; determining a crossing TI from the intersection of the recovery curves and the respective TI; and calculating an optimal TI from the crossing TI.

In a second aspect, a system for automatically calculating an optimal inversion time (TI) for flow independent dark-blood delayed enhancement (FIDDLE) is provided. The system includes a magnetic resonance scanner and a control unit. The magnetic resonance scanner is configured to acquire FIDDLE TI-scout data, the FIDDLE TI-scout data comprising a series of phase sensitive FIDDLE images, each having a different TI, and a series of phase reference images, each of which are associated with one phase sensitive FIDDLE image of the series of phase sensitive FIDDLE images. The control unit is configured to segment the series of phase sensitive FIDDLE images into a myocardial wall compartment and a blood pool compartment, using the series of phase reference images to derive the segmentation contours for the phase sensitive FIDDLE images, calculate, from the myocardial wall compartment, a signal of normal myocardium in each of the phase sensitive FIDDLE images, calculate, from the blood pool compartment, a signal of blood in each of the phase sensitive FIDDLE images, group each pair of the normal myocardium signal and its respective TI into a signal-versus-TI function that represents a recovery curve of normal myocardium, group each pair of the blood signal and its respective TI into a signal versus-TI function that represents a recovery curve of blood, determine a crossing TI from an intersection of the recovery curves and the respective TI, and determine the optimal TI from the crossing TI.

In a third aspect, a method for segmenting a series of phase sensitive FIDDLE images into a myocardial wall compartment and a blood pool compartment is provided. The method includes: generating, using a style transfer network, synthetic FIDDLE reference (REF) images; training, using the synthetic FIDDLE REF images, a segmentation neural network for segmenting image data into the myocardial wall compartment and the blood pool compartment; finetuning the segmentation neural network using a dataset of real FIDDLE REF images; and applying the trained segmentation neural network to the series of FIDDLE REF images and transferring the obtained segmentation to the phase sensitive FIDDLE images, to output the segmented myocardial wall compartment and blood pool compartment.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Embodiments described herein provide systems and methods for automatically selecting an optimal inversion time (TI) for Flow-Independent Dark-blood Delayed Enhancement (FIDDLE). For a FIDDLE imaging procedure, FIDDLE TI-scout images are segmented into the blood pool and the myocardium region. Phase-sensitive inversion recovery (PSIR) pixel intensity features of the blood and the myocardium are calculated for the FIDDLE TI-scout images to infer the blood and the normal-myocardium recovery curves. The intersection of these curves (TIcross) is determined and used as a reference TI referred to as the crossing TI, from which the optimal TI is calculated.

The disclosed embodiments may be implemented to computationally facilitate processing of medical imaging data and consequently improving and optimizing medical diagnostics. Embodiments leverage the power of artificial intelligence (AI) to enhance the process of LGE procedures.

Figure 1:
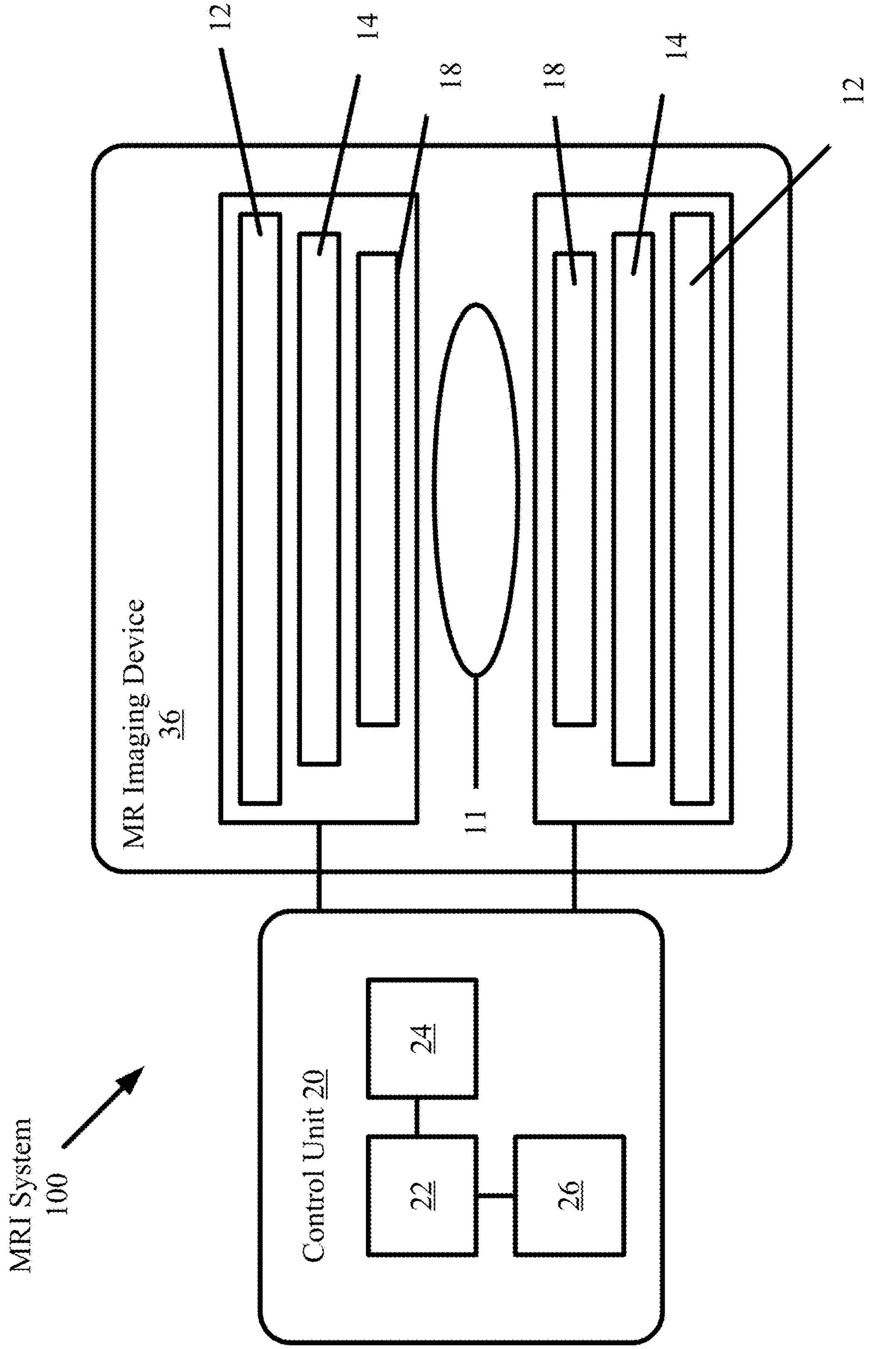
FIG. 1 depicts an MR system 100 according to an embodiment.

FIG. 1 depicts an example magnetic resonance (MR) system 100 that may be used for acquisition of magnetic resonance imaging (MRI) data. The MR system 100 includes a control unit 20 configured to determine a set of sequences for a whole body MRI screening procedure for a patient. The control unit 20 is further configured to process the MR signals and generate images of a portion or entirety of the patient for analysis and/or display to an operator, for example, using a processor 22. The control unit 20 may store the MR signals and images in a memory 24. The control unit 20 may include a display 26 for presentation of images to an operator. The control unit 20 is configured to analysis the MR signals and images in order to adjust the set of sequences while the screening procedures proceeds. The control unit 20 is further configured to interpret the MR signals and images. The MR scanning system 100 is only exemplary, and a variety of MR scanning systems or other imaging systems may be used to collect the imaging data. In addition, alternative medical imaging modalities may be used for acquisition. Different parameters, settings, locations, etc. may be used with the techniques described herein.

In the MR system 100, magnetic coils 12 create a static base or main magnetic field $B_0$ in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18. The RF coil 18 produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g. signals from the excited protons within the body as the protons return to an equilibrium position established by the static and gradient magnetic fields. The MR signals are detected and processed by a detector within RF module and the control unit 20 to provide an MR dataset to a processor 22 for processing into an image. In some embodiments, the processor 22 is located in the control unit 20, in other embodiments, the processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a Cartesian or other spatial acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field generator acquires individual frequency components in an order corresponding to a sequence of substantially adjacent individual data elements in the array, and magnetic field gradient change between successively acquired frequency components is substantially minimized.

The MR system 100 may be configured to acquire medical imaging data (MR data) using Late gadolinium enhancement (LGE). LGE is an imaging method where MR data is obtained after the administration of gadolinium contrast material that accumulates into a tissue with increased extra cellular space. LGE is based on the shortening of T1 and different regional distribution patterns of the gadolinium-based contrast material within the extracellular space of the myocardium. LGE also depends on varying uptake and washout patterns within the normal myocardium and those different disease processes. The T1-weighting is achieved by an inversion recovery (IR) pulse and a data acquisition (DA) timed to this pulse so that the recovery curve of normal, i.e., viable, healthy myocardium passes through the zero-magnetization point resulting in dark normal myocardium but bright infarcted, i.e., dead myocardium.

Figure 2:
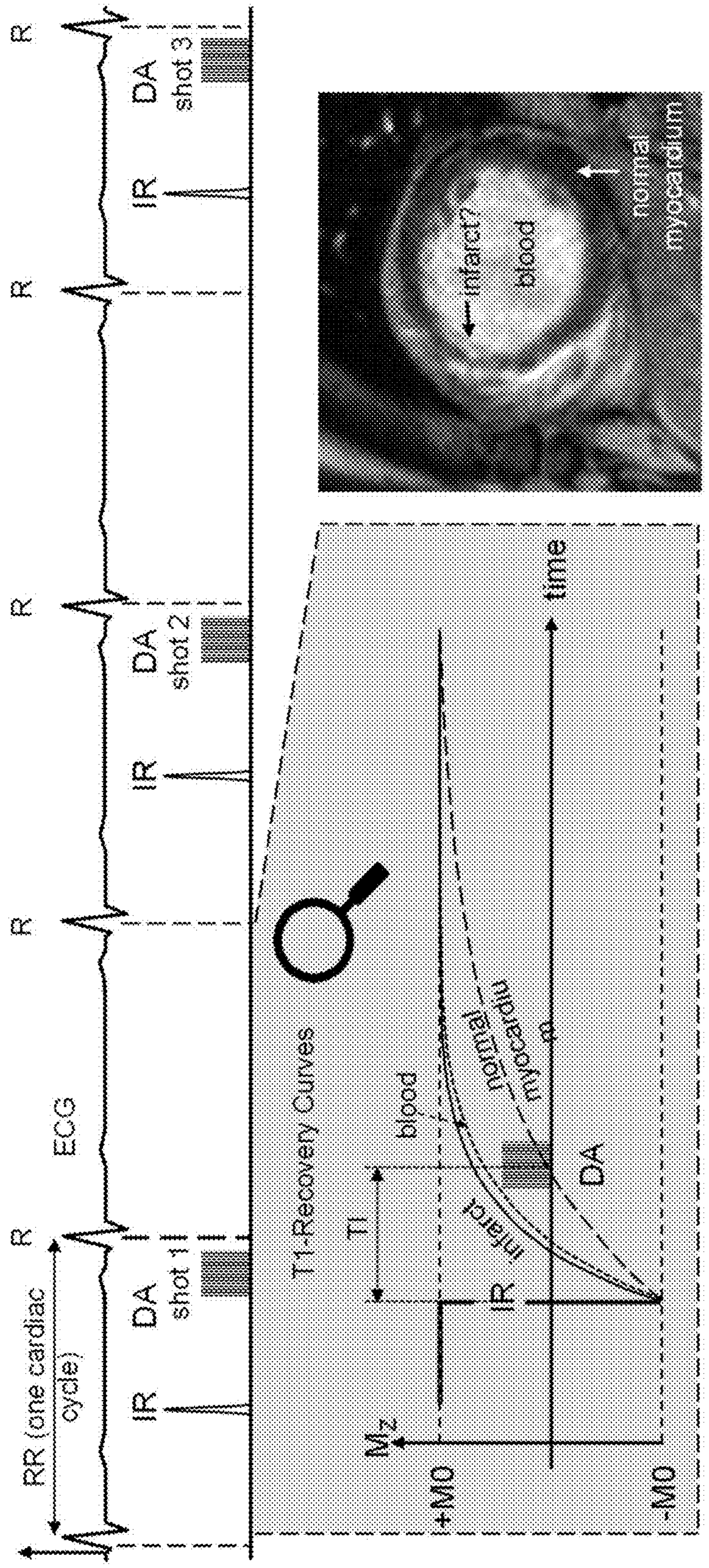
FIG. 2 depicts a standard IR sequence for LGE.

FIG. 2 shows a section of a standard segmented IR sequence for LGE, the resulting T1-recovery curves of normal myocardium, infarct, and blood, and a typical LGE image produced by such a sequence. The MR system 100 acquires a set of raw data lines in diastole. Since a single DA set is insufficient to fill the entire raw data space (k-space), each DA "shot" acquires only a fraction referred to as a segment (not to be confused with the AI-powered segmentation of images), and the data of all shots is combined to create a full k-space at the end of the acquisition. This k-space data is then subjected to a Fast Fourier Transform (FFT) to yield an MR image. The prior IR pulse is timed by the inversion time (TI) to the acquisition of the line closest to the center of k-space so that the T1-recovery curve of normal myocardium has approximately zero magnetization when this center line is acquired. This is known as myocardial "nulling". At that point in time, infarct and blood have much higher signal and therefore appear bright in the MR image on the right, whereas normal myocardium appears dark. The data in the center of k-space determines the brightness and contrast of the image. By capturing the signals of normal myocardium and infarct at that time, significant infarct to-normal contrast is created.

This bright-blood LGE provides excellent image contrast between normal myocardium depicted in dark grey (depending on the specific TI used) and the "hyperenhanced", i.e., bright, infarct. But the contrast between infarct and blood pool is often poor, also seen in the MR image on the right. Due to the equally high signal of the blood pool and infarcted tissue and scar, subendocardial hyperenhanced regions may not be recognized as such. In the MR image of FIG. 2, it is not clear whether the septal endocardial region is infarcted or simply consists of thinned but viable myocardium.

Figure 3A:
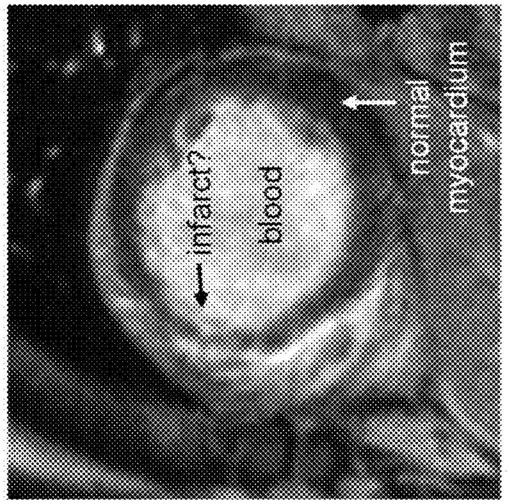
FIG. 3A depicts a conventional (bright-blood) LGE image.
Figure 3B:
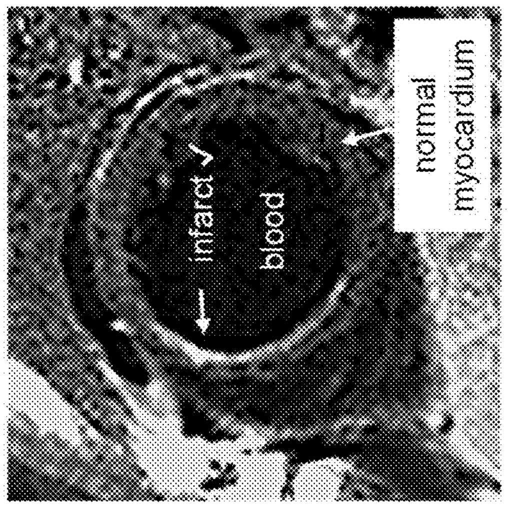
FIG. 3B depicts a FIDDLE (dark-blood) image.

A technique referred to as Flow-Independent Dark-blood DeLayed-Enhancement (FIDDLE) is used to solve this problem by its dark depiction of the blood pool while showing infarct bright and normal myocardium dark grey. FIG. 3A depicts the same conventional (bright-blood) LGE image as in FIG. 2 where the infarct cannot be differentiated from the blood pool. FIG. 3B depicts a FIDDLE (dark-blood) image of the same patient and slice location where the thin subendocardial septal infarct is clearly visible.

Setting an optimal TI for the FIDDLE sequence is even more important than for bright-blood LGE. The optimal TI herein refers to a reference TI value that provides a standardized contrast between different substances/materials. Different operators may have difference preferences when analyzing MR images. Thus, the term "optimal" refers to reference value rather than specifically optimal for any operator. However, given the optimal TI value for a procedure, an operator may adjust the optimal TI to their own preferences. More particularly, the term "optimal TI" herein refers to the TI that offers a high contrast between blood, normal-myocardium and infarcted-myocardium, which provides an ideal contrast between the three substances to enable the identification of infarcted myocardium, TIopt. TIopt is computed by subtracting a time value from the crossing TI. The crossing TI refers to the intersection of the blood and the normal-myocardium recovery curves (the TIcross). While the optimal TI is subjective, the crossing TI can be objectively defined based on the intersection of the blood and the normal-myocardium recovery curves. In prior usage, determining the optimal TI requires significant clinical experience due to the inherent variability of the contrast agent concentration and resulting T1 in tissue and blood, which is a function of the patient-specific contrast clearance, the time after the injection, the injected dose, and the specific contrast agent used. For example, the T1 of blood is different in every patient, and so is the T1 of normal myocardium resulting in the operator to determine an optimal TI for each procedure/patient. Using the optimal TI specifically determined based on the FIDDLE TI-scout will produce more consistent imaging results across all patients/procedures/etc.

Figure 4:
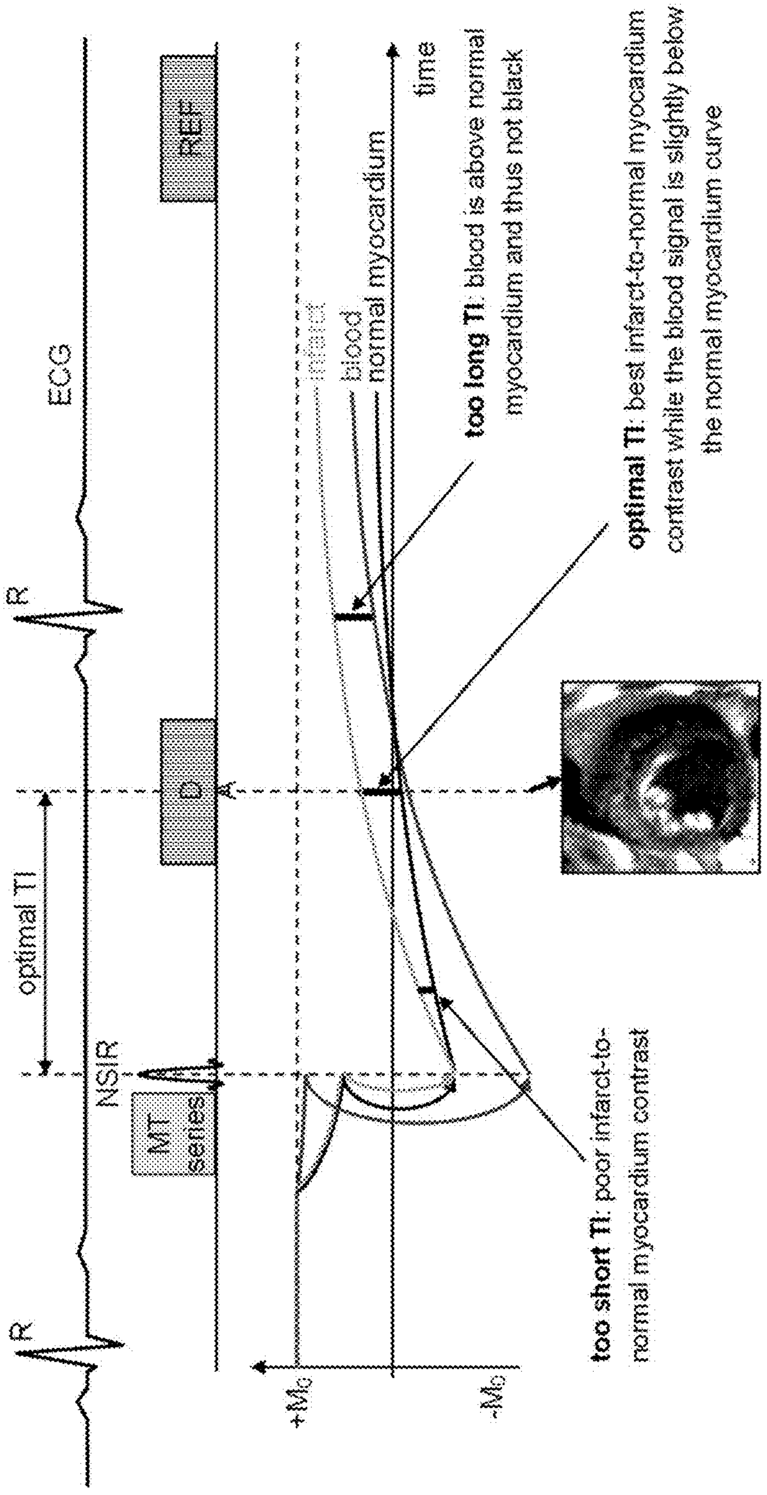
FIG. 4 depicts an example section of a FIDDLE sequence.

FIG. 4 depicts an example FIDDLE sequence (a section acquiring a portion of the entire data needed for one FIDDLE image), the resulting T1-recovery curves of normal myocardium, infarct, and blood, and a FIDDLE image produced for the optimal TI. FIDDLE has two distinct features that set it apart from conventional bright-blood LGE. First, a series of magnetization transfer (MT) pulses is played in addition to, and immediately before, the IR pulse. This MT series saturates normal and infarcted myocardium alike, while having little effect on blood, for example as depicted in the magnetization curves of FIG. 4. Thereby, the magnetization of tissue and fluid are separated. The ensuing IR pulse globally inverts all magnetization so that the recovery curves of tissue and blood have different starting points. Second, reference (REF) data is acquired in the heartbeat following the MT-IR data beat, in the same cardiac phase. REF data allows reconstructing an MT-IR image wherein each pixel reflects the true value of the magnetization, i.e., the value of the curve including its sign, rather than only its magnitude. This method is known in the art as phase-sensitive inversion recovery (PSIR). It is an option for standard LGE but a requirement for FIDDLE. Conventional LGE images are magnitude images with a grey scale where zero magnetization is depicted as dark and both the most positive and most negative magnetization as bright. In distinction, PSIR images present the pixels with the smallest magnetization as the darkest, regardless of their sign and actual value. To reconstruct the true sign, a prior sign restauration/phase correction is required, for which the REF data is needed. PSIR is required for FIDDLE since the MT-IR preparation with an optimal TI puts the magnetization of blood, normal myocardium, and infarct in such an order that blood is the smallest and infarct the brightest. Thereby, it intrinsically creates dark blood in the PSIR image, but not in a magnitude image. Blood is darkest in FIDDLE images not because it has zero magnetization, but because blood has the smallest magnetization in the image. This is different to the classic double-IR dark-blood preparation that creates zero-magnetization of blood, which appears black in a magnitude image. As seen in FIG. 4, a TI for which blood signal is just slightly below normal myocardium signal is considered optimal, as it ensures dark blood while simultaneously allowing the infarct magnetization to recover as long as possible to maximize the infarct-to-normal myocardium contrast. Depending on the patient specific T1 values of blood and normal myocardium at the time of imaging, the magnetization of blood can be negative, zero, or positive. Regardless, blood will always be depicted dark in the FIDDLE image as long as its magnetization is below that of normal myocardium.

Determining the optimal TI may be tedious. Traditionally, the MR operator uses an initial guess for TI and acquires a breath-held segmented FIDDLE image. Depending on the initial image contrast, the operator repeats the acquisition with a shorter TI if the blood was not black, or a longer TI if the contrast between normal myocardium and blood was too big. Sometimes, two time-consuming attempts (two breath holds) are needed to find the optimal TI.

Figure 5:
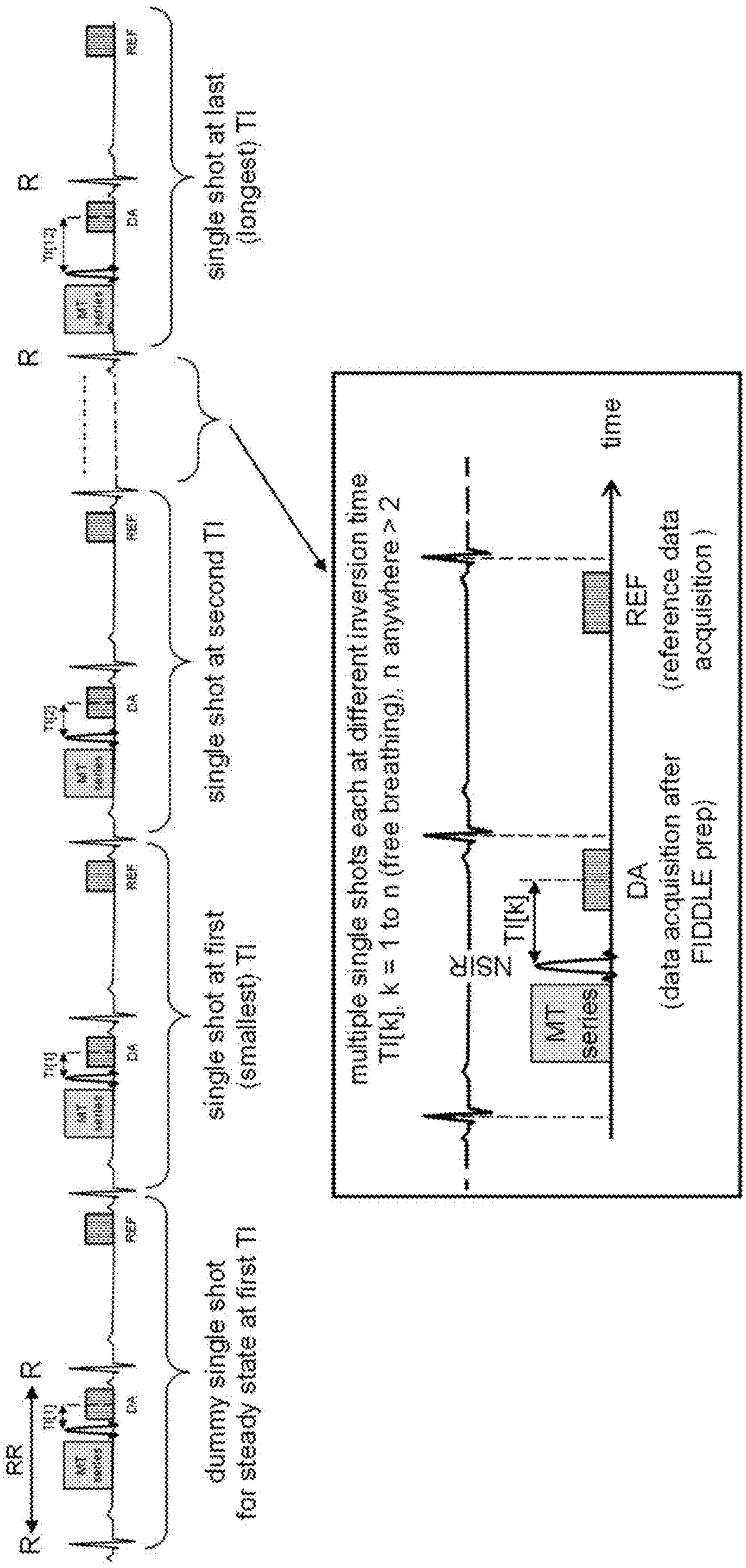
FIG. 5 depicts a single-shot FIDDLE TI-scout sequence.
Figure 6:
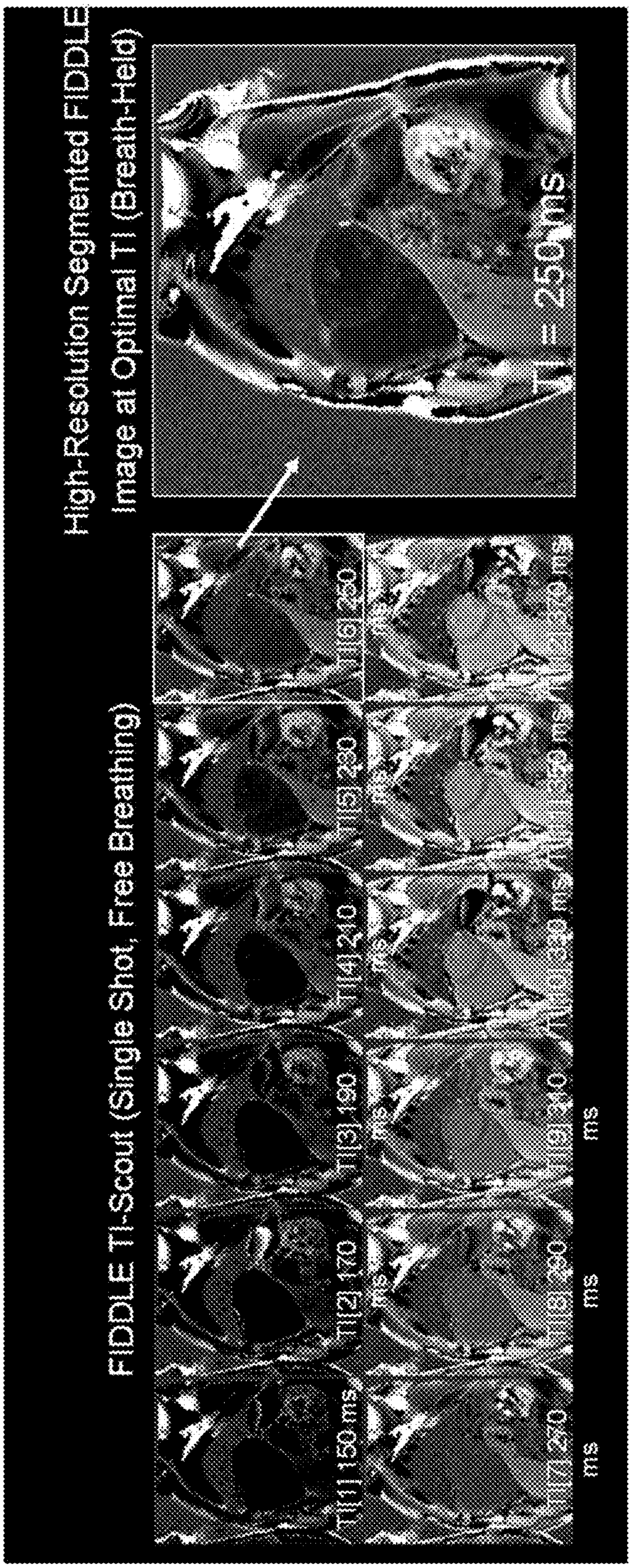
FIG. 6 depicts a series of single shot FIDDLE images.

One alternative method for finding an optimal TI uses a single-shot FIDDLE TI-scout sequence. FIG. 5 depicts such a sequence. Each DA and subsequent REF are reconstructed into a single-shot FIDDLE image. The FIDDLE image is always a phase-sensitive inversion recovery (PSIR) image. For each DA, the TI is slightly altered, typically increased by 10 ms to 20 is, so that a series of single-shot FIDDLE TI-scout images with different TI values is produced. A typically covered range of TI values goes from 150 ms to 370 ins in 20 ms increments as depicted in FIG. 6. The number of lines in each DA is the same for the TI-scout and the segmented FIDDLE sequence for which TI is sought. Also, other magnetization-affecting parameters such as the readout flip angle, echo spacing, and trigger pulse are exactly matched between the FIDDLE TI-scout and the subsequent segmented FIDDLE sequence. This ensures that the magnetization of the scout and the segmented sequence behave the same way so that the TI-scout and the segmented FIDDLE image have identical image contrast for the same TI. The operator browses through the series of scout images and selects the one with the optimal contrast, for example the image with TI=250 ms in the context of FIG. 6. The TI of that image is then used to acquire the breath-held segmented FIDDLE image. The single shot FIDDLE TI-scout sequence produces PSIR and magnitude images, unlike conventional TI-scout methods that only produce magnitude images. This single-shot TI-scout sequence reconstructs REF images in addition to the FIDDLE (PSIR) images, which are instrumental for the herein disclosed segmentation step of certain embodiments as described herein.

Finding the optimal TI by browsing through the TI-scout images is time consuming. For example, the brightness and contrast of each TI-scout image often has to be individually adjusted to determine which image has the desired contrast. Furthermore, the personal preference for the optimal FIDDLE image contrast varies between operators, leading to poor reproducibility of FIDDLE contrast across technologists and patients. An automatic optimal TI determination, that is faster and also consistent across operators, systems, and patients, would be very useful.

Figure 7:
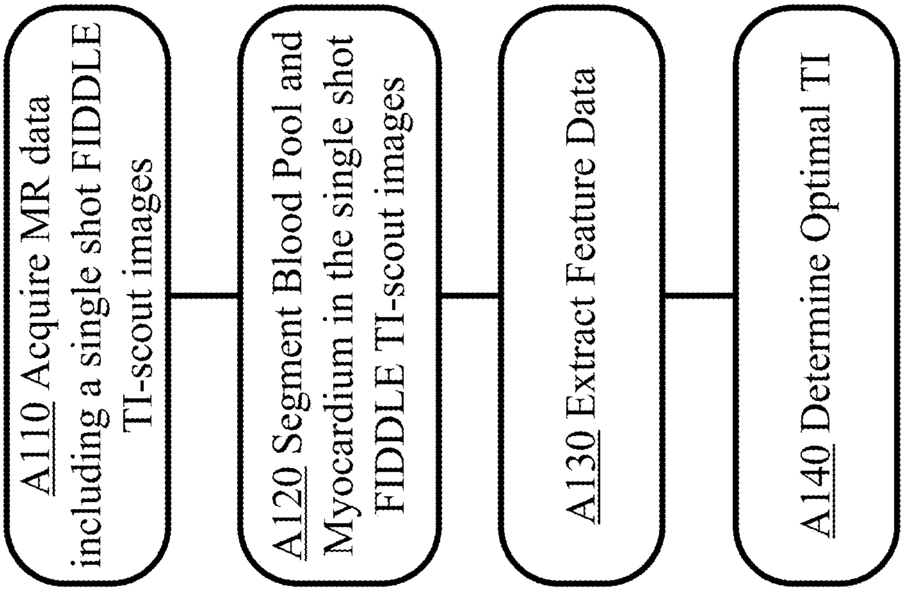
FIG. 7 depicts an example workflow for determining an optimal TI value according to an embodiment.

FIG. 7 depicts an example workflow for determining an optimal TI value. In the embodiments described herein, the method automatically calculates an optimal TI (e.g., using a TIcross reference value) for a segmented FIDDLE acquisition, using a series of FIDDLE TI-scout images including REF images as input. Embodiments use deep learning to train a network to perform myocardium segmentation on REF images associated with FIDDLE TI-scout images. Since prior segmentation networks typically only work on cine-type magnitude but not on REF images, embodiments apply a style transfer to cine images to generate synthetic REF images on which the network is then trained. This dramatically improves the segmentation performance on FIDDLE TI-scout images. A separate network is trained to find the intersection of the recovery curves of normal myocardium and blood pool. This network takes the FIDDLE TI-scout images and the myocardium and blood pool segmentation as input and produces the TI where the intersection occurs, TIcross, as output. The acts are performed by the system of FIG. 1, 9, 15, other systems, a workstation, a computer, and/or a server. Additional, different, or fewer acts may be provided. For example, the TIcross value may be used as a reference to compute an operator specific TI value based on the operator's preferences. The acts are performed in the order shown (e.g., top to bottom) or other orders.

In Act A110, MR data is acquired including a series of FIDDLE TI-scout images including the REF images. The MR data may be acquired by the MR system of FIG. 1 or other system. In operation, the MR system 100 acquires a series of short-axis single-shot FIDDLE TI-scout images. The MR System 100 is configured to generate a series of magnetization transfer (MT) pulses in addition to, and immediately before, an IR pulse. This MT series saturates normal and infarcted myocardium alike, while having little effect on blood. Thereby, the magnetization of tissue and fluid are separated. The ensuing IR pulse globally inverts all magnetization so that the recovery curves of tissue and blood have different starting points. Reference (REF) data is acquired in the heartbeat following the MT-IR data beat, in the same cardiac phase. REF data allows reconstructing an MT-IR image wherein each pixel reflects the true value of the magnetization, i.e., the value of the curve including its sign, rather than only its magnitude. This method is known in the art as phase-sensitive inversion recovery (PSIR). PSIR images present the pixels with the smallest magnetization as the darkest, regardless of their sign and actual value.

In Act A120, the blood pool and myocardium are automatically segmented in the series of FIDDLE. TI-scout images including the REF images. This comes with the challenge that the myocardium and blood pool intensities and contrast are changing throughout the FIDDLE scout series. Moreover, contrast between myocardium and blood pool is greatly reduced for TI values close to the optimal TI. Therefore, blood pool localization and segmentation of blood and myocardium in the FIDDLE (PSIR) images fails or is imprecise when using the existing technology. To overcome the problem of a small blood-to-myocardium contrast, embodiments process the REF images for segmentation instead of the PSIR or magnitude images. All REF images have identical image contrast since no magnetization preparation is played out before their acquisition. This makes it possible for the segmentation network to detect the endo- and epicardial borders. This process is not used in previous methods since the conventional TI-scout sequence creates no PSIR and no REF images.

Any method for segmentation may be used. For example, segmentation may be thresholding-based, region-based, shape-based, model based, neighboring based, and/or machine learning-based among other segmentation techniques. Thresholding-based methods segment the image data by creating binary partitions based on image attenuation values, as determined by the relative attenuation of structures on the images. Region-based segmentation compares one pixel in an image to neighboring pixels, and if a predefined region criterion (e.g., homogeneity) is met, then the pixel/voxel is assigned to the same class as one or more of its neighbors. Shape-based techniques use either an atlas-based approach or a model-based approach to find a lumen boundary. Model-based methods use prior shape information, similar to atlas-based approaches; however, to better accommodate the shape variabilities, the model-based approaches fit either statistical shape or appearance models of the heart to the image by using an optimization procedure. The output of segmentation may be one or more masks that describe different substances or structures.

In an embodiment, a neural network or other machine trained model may be used for segmentation. The machine learned network(s) or model(s) used to segment the FIDDLE data (and other functions described herein) may include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes.

The neural network/model may be configured using a machine training method and training data. The training data may be acquired at any point prior to inputting the training data into the model. Different models may be configured for different tasks, for example, different models for determining features and segmentation. The output of certain models may be used by other models for determining certain relevant features. For example, one machine trained model may perform segmentation while another may use the output of the segmentation to derive values or provide classification for a particular relevant features. For training and applying a machine trained model there are two stages, a training stage for generating or training the model using a collection of training data and an application stage for applying the generated/trained entity matching network to new unseen (unlabeled) data. The training stage includes acquiring training data during patient scans, processing the training data, and inputting the training data into the model in order to generate a trained model. The output is a trained model that is applied in the application stage. The application stage includes receiving real-time FIDDLE data from, for example, a MR scout scan, and applying the trained model that was trained during the training stage to segment the image data. The training stage may be performed at any point prior to the application stage. The training stage may be repeated after new training data is acquired. The application stage may be performed at any point after the training stage generates the trained network and real-time data is received.

One challenge with segmenting the myocardium in the FIDDLE TI-scout images by a neural network is that the contrast between the myocardium and blood pool dynamically changes as function of TI, making the detection of the endocardial border difficult. This especially applies to TI-scout images close to the crossing point TIcross. With prior art segmentation approaches the endocardial boundary cannot be reliably detected.

To circumvent this problem, Embodiments use the FIDDLE REF images for the myocardium segmentation instead of FIDDLE TI-scout (FIDDLE images are always PSIR images) or magnitude images. The derived myocardium and blood pool masks are then transferred to the FIDDLE images. These REF images have an image contrast independent of the TI used for its respective MT-IR image. In addition, the REF images have a contrast appearance similar to cine images, for which large amounts of annotated training data already exist, which alleviates difficulties in training the network. However, directly using a prior art segmentation network trained on cine images to segment FIDDLE REF images may yield insufficient segmentation quality. Embodiments improve the segmentation accuracy in the existing network pre-trained on cine images by finetuning the network on a set of annotated REF training images. Alternatively, a style transfer may be applied to cine images for generating synthetic REF images on which the neural network is then trained. This also improves the segmentation performance on FIDDLE TI-scout images.

Another challenge is that few REF images are available for training and even fewer REF images with a manual myocardium ground truth segmentation. Manual segmentation is generally labor intensive and time consuming. Having to produce large amounts of annotations for the same anatomical structure for each new type of MR image acquisition is unfeasible. Embodiments address this challenge by using a style transfer approach that leverages a large dataset of existing manual myocardium segmentation performed for a different type of cardiac MR acquisition (for example cine balanced steady-state free precession—bSSFP). By this it minimizes the need for extensive annotation of FIDDLE REF images. An alternative approach includes pre-training a model on a large amount of annotated cine images. Only a small number of annotated REF image are then used for finetuning the final segmentation network.

Figure 8A:
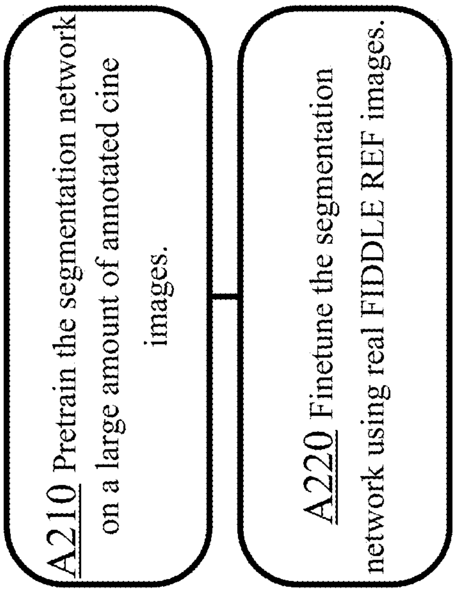
FIGS. 8A and 8B depict example workflows for training the segmentation network according to embodiments.
Figure 8B:
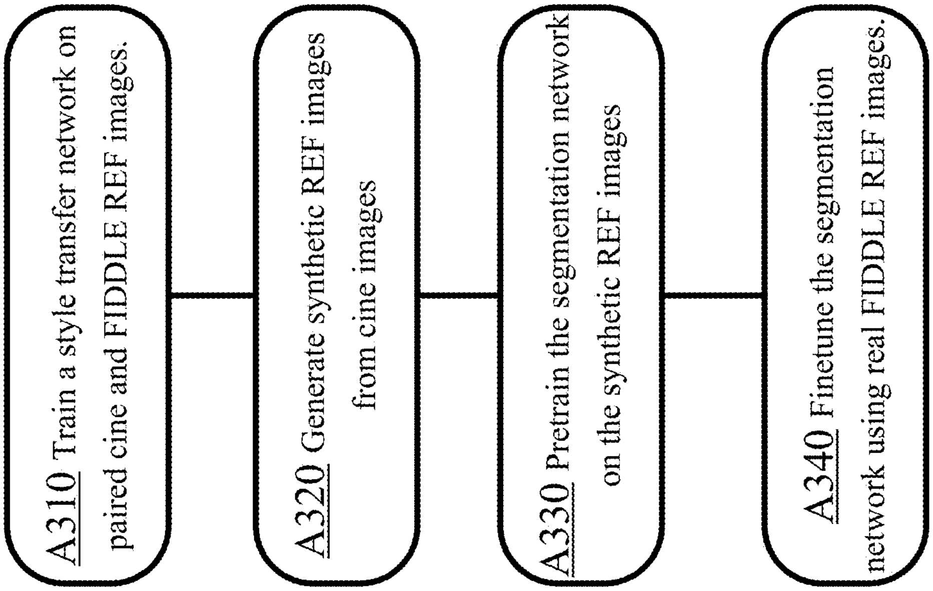

FIGS. 8A and 8B depict examples for training the segmentation network. In FIG. 8A, the segmentation network is trained using cine and FIDDLE REF images according to the following steps. In act A210, the segmentation network is pretrained on a large amount of annotated cine images. In act A220, the segmentation network is finetuned using real FIDDLE REF images.

In FIG. 8B, the segmentation network is trained using synthetic and real FIDDLE REF images according to the following steps. In act A310, a style transfer network is trained on paired cine and FIDDLE REF images. Style transfer takes two images, for example a content image and a style reference image, and blends them together so the output image looks like the content image, but including the style of the style reference image. After training, this network can transform cine images (as input) into synthetic REF images (as output). In act A320, synthetic REF images are generated from cine images, e.g. from the publicly available images from the UK Bio Bank database (UKBB). In act A330, the segmentation network is pretrained on the synthetic REF images generated in act A320. In act A340, the segmentation network is finetuned using real FIDDLE REF images.

Figure 9:
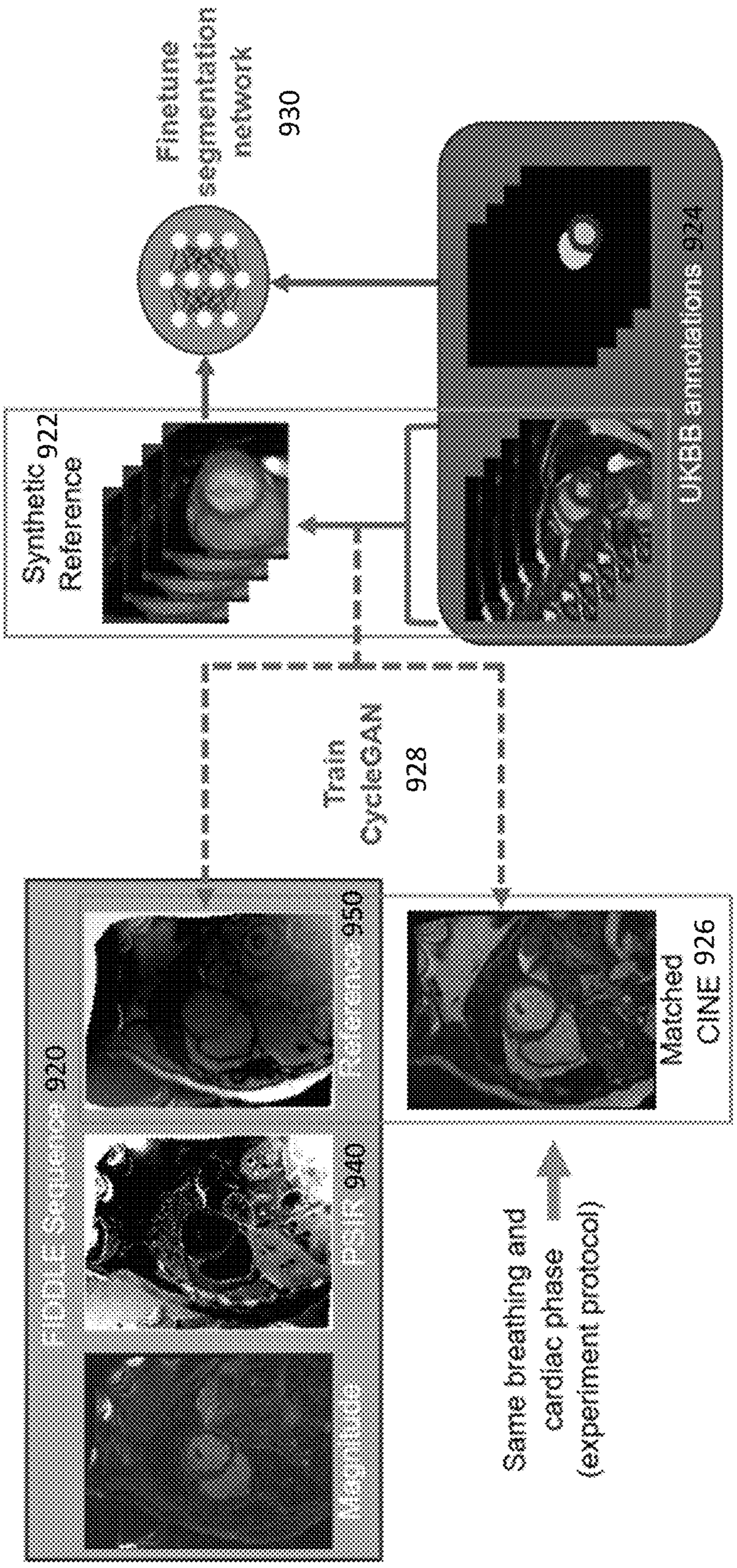
FIG. 9 depicts an example of the method of FIG. 8B that uses a CycleGAN for the style transfer network according to an embodiment.
Figure 10A:
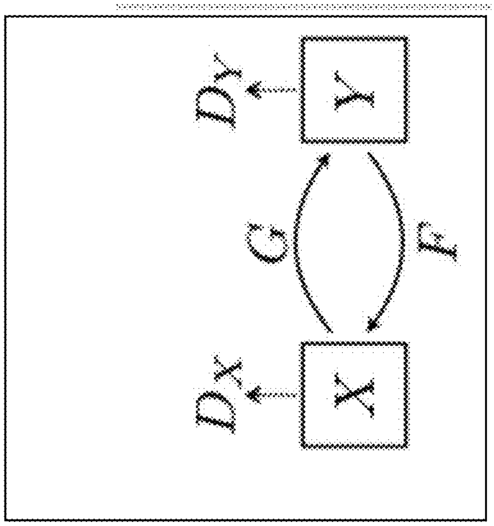
FIGS. 10A, 10B, and 10C depicts examples of a CycleGAN according to an embodiment.
Figure 10B:
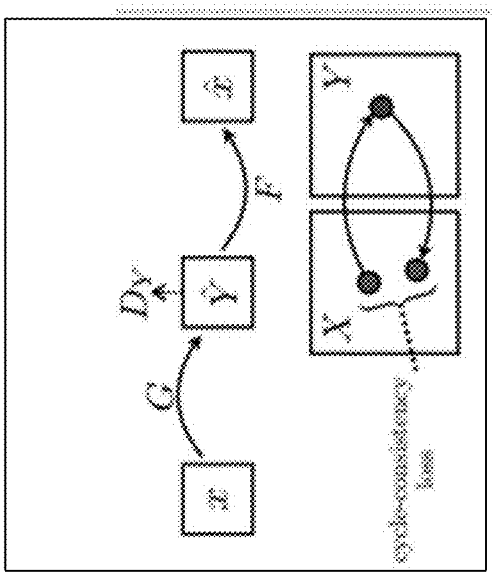
Figure 10C:
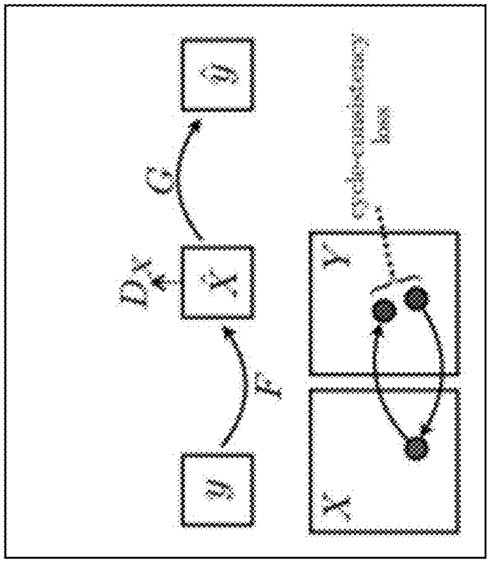

One architecture of the style transfer network of act A310 may be a CycleGAN. FIG. 9 depicts an example of the method of FIG. 8B that uses a CycleGAN for the style transfer network. In FIG. 9, a FIDDLE sequence 902 including magnitude images, PSIR images 940, and reference images 950 is used to train a CycleGAN 928 along with matched cine images 926 and UKBB annotations 924. Synthetic reference images 922 are generated by the CycleGAN 928 and used with the UKBB annotations 924 to train and finetune the segmentation network 930. The CycleGAN architecture uses a cycle consistency loss, through which the network learns a bijective mapping between the two domains. Unlike in typical training pipeline where the paired images are randomly selected from both datasets, the learning procedure pairs images from the same acquisition only. The loss function used is the weighted sum between adversarial loss and cycle consistency loss. FIGS. 10A, 10B, and 10C depicts examples of a CycleGAN and how it operates. As depicted in FIG. 10A, the CycleGAN includes two GANs, each of them containing a generator (G and F) and a discriminator (Dx and Dy). The purpose of the first GAN is to generate synthetic REF images given an acquired cine image. The purpose of the second GAN is to generate synthetic cine images given acquired REF images. In FIGS. 10B, and 10C, the generator G is given as input a cine image and produces synthetic REF image. Generator F is given as input a REF image and produces a synthetic cine. The discriminators Dx and Dy try to distinguish between the synthetic and real images in the cine and REF domains, respectively. In one training step, G generates synthetic REF image from a real cine image. The synthetic REF image is then fed back as input to F which generates a synthetic cine image. In the converse training step, F generates synthetic cine image from a real REF image. The synthetic cine image is then fed back as input to G which generates a synthetic REF image.

The CycleGAN network may be pre-trained, for example, in cases where the training dataset of paired acquired breath-hold REF and cine images is relatively small. Since the amount of paired cine-REF images is small, in another embodiment, the style transfer network may be pretrained on pairs of cine and synthetically generated REF images. Starting from cine images REF images are artificially generated by applying a defocus blur, shifting with a small offset and linear transformations to reduce the contrast. Analogously, the same operations may be applied, with different parameters, for the other direction. A pre-trained contrast-enhancement model may also be employed.

Figure 11:
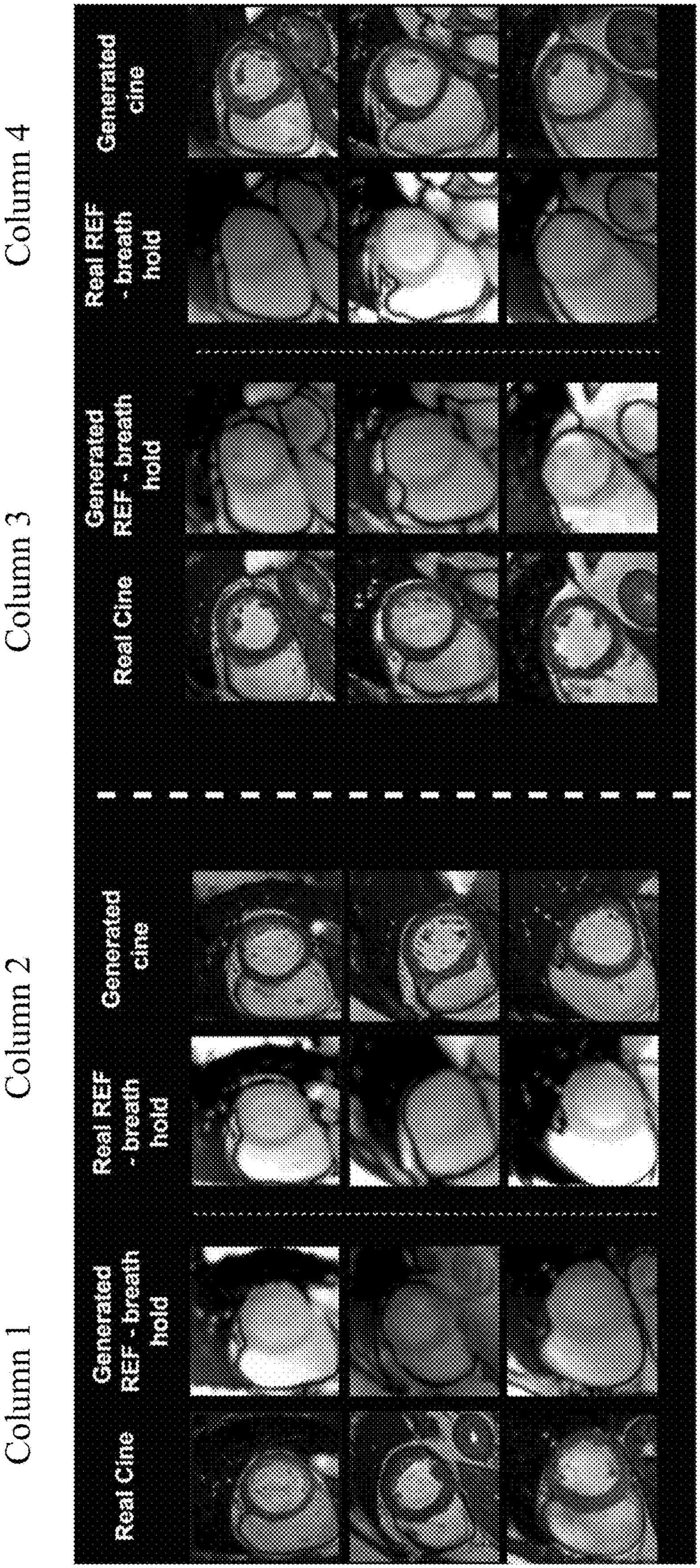
FIG. 11 depicts example results created by a style transfer network for six pairs of images according to an embodiment.

FIG. 11 depicts example results created by a style transfer network for six pairs of images (three examples on the left half, three on the right). The translation of images from one domain to the other is shown, in both directions. The first two columns 1 and 2 show the forward translation from an acquired diastolic cine image to a synthetic breath-hold REF image (also diastolic). Columns 3 and 4 show the reverse translation from an acquired REF image to a synthetic diastolic cine image. The contours derived from the REF images are then transferred to the PSIR images. That is possible because each pair of PSIR and REF image was acquired in close temporal proximity.

In an alternative embodiment, a neural network may be used directly on the FIDDLE TI-scout images without the explicit segmentation step. This may reduce the computational complexity of the workflow, but may result in lower quality results. In an embodiment, additional compartments or substances may be segmented other than the myocardium and blood pool. Features for the additional segmentations/masks may be derived below along with the myocardium and blood pool signals. The additional features/signals may be used to compute the optimal TI.

Figure 12:
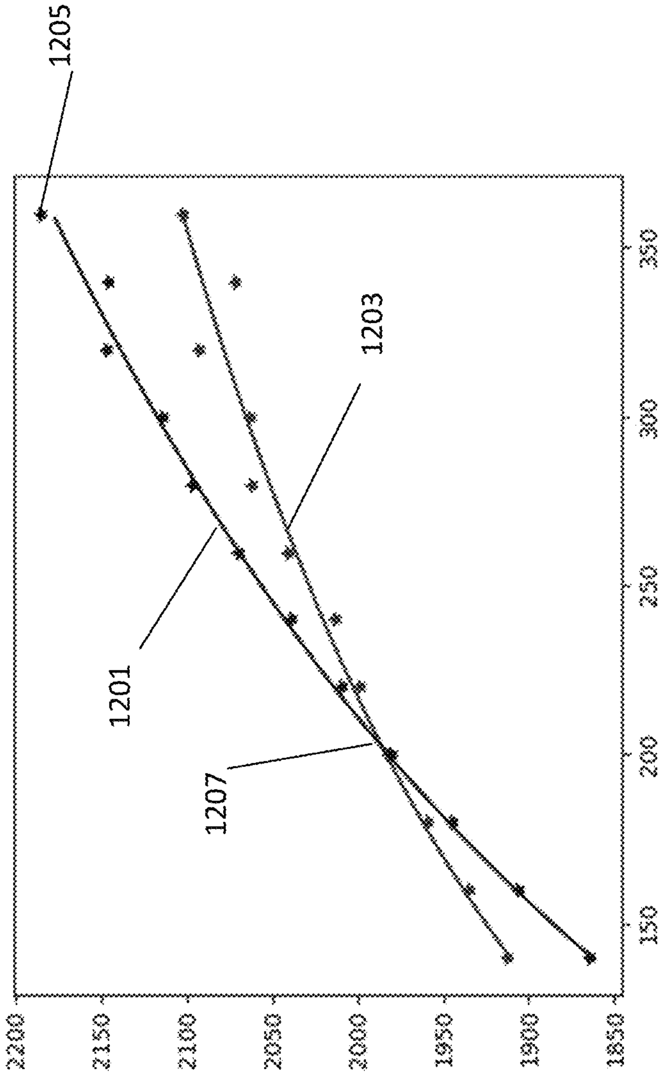
FIG. 12 depicts an example of computed feature data points according to an embodiment.

Referring back to FIG. 7, at Act A130, features are computed for the myocardium and blood pool. For example, the MR system 100 computes pixel intensity features (median, lower quartile, upper quartile) for the myocardium and blood pool separately from the FIDDLE (PSIR) images. Each intensity feature is computed for every image frame in the scout image series as a function of TI. FIG. 12 depicts an example of computed feature data points. Each star 1205 represents the measured feature sample for either the blood pool or the myocardium in the respective TI-scout image. The PSIR-specific pixel scaling always assigns a value of 2048 for zero-magnetization, smaller values for negative and larger for positive magnetization. In an embodiment, the signal of normal myocardium is computed as a lower quartile of all pixels contained in the myocardial wall compartment. In another embodiment, the signal of normal myocardium is computed as a median pixel intensity of all pixels contained in the myocardial wall compartment. In another embodiment, the signal of a blood pool is extracted as the mean pixel intensity of all pixels contained in the blood pool compartment. In yet another embodiment, the signal of a blood pool is extracted as the median pixel intensity of all pixels contained in the blood pool compartment.

Figure 13:
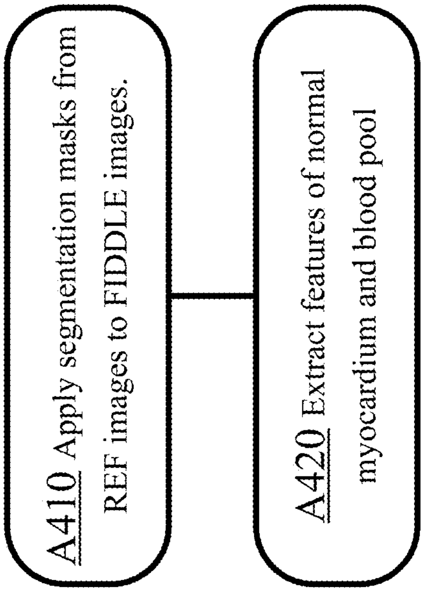
FIG. 13 depicts an example workflow for extracting features from the segmented myocardium and blood pool according to an embodiment.

FIG. 13 depicts an example workflow for extracting features from the segmented myocardium and blood pool of Act A120. At Act A410, the segmentation masks obtained from the REF images are applied to the corresponding FIDDLE images. At act A420, feature of the normal myocardium and blood pool are extracted. In an embodiment, this results in a series of N feature vectors, where N is the number of TI-scout images in the FIDDLE TI-scout series. To fill each feature vector, a set of statistical measures is computed, for example the lower quartile, the median, and the upper quartile of the pixel intensities in the masked region of interest for myocardium respectively blood. In this embodiment, each PSIR image is described by six numerical values, three for the myocardium and three for the LV blood pool, placed into one feature vector.

In FIDDLE TI-scout images including myocardial infarction, the segmentation mask comprising the myocardial wall includes normal as well as infarcted myocardium. By extracting the lower and upper quartile measure from the myocardium segmentation mask, as opposed to simply computing the average, embodiments estimate the intensity of the normal, darker myocardium, and the brighter infarct. If a small to medium infarct is present in the myocardium at the location where the FIDDLE TI-scout was acquired, it will likely not affect the lower quartile, potentially slightly increase the median, and likely affect more the upper quartile, which will have a higher value compared to when no infarct was present. A very small infarct would not affect the TI prediction, even if the average of the entire myocardium intensity was directly considered. The FIDDLE scout may be acquired at a position where a significant amount of normal myocardium is present. However, embodiments may not cover the case when (almost) only infarcted tissue or scar is visible with no normal myocardium. This case is physiologically extremely unlikely and therefore purely theoretical. The lower quartile feature may then be used as a surrogate measure of the normal myocardium intensity to identify the crossing TI though a numerical method as described below in Act A140. Alternatively, the upper quartile, median, and lower quartiles can be used together in a feature vector by a neural network to regress the crossing TI as described below in Act A140.

At Act A140, the optimal TI is determined from the normal myocardium and blood pool feature curves. Embodiments may determine the intersection of both curves in multiple ways. In one embodiment, a neural network takes the star data points (for example as depicted in FIG. 12) as input and provides the crossing TI, TIcross, as output. As shown in FIG. 12, there are two curves derived from the data points 1205. The normal myocardium curve 1203 and the blood pool curve 1201. The intersection of these two curves is the TIcross 1207 value. In another embodiment, the optimal TI is determined by using the two recovery curves and fitting a curve to the data points, for example by a logarithmic or piecewise linear fit. The crossing TI, TIcross 1207 is the intersection of both curves. At the respective TI value, TIcross 1207, blood and normal myocardium have equal intensity in the FIDDLE image. This is a user-independent, objective assessment, from which a user-preferred, subjective optimal TI may be calculated. In previous methods only the normal myocardium is typically examined but not the blood. These prior methods do not look for an intersection of curves but merely find the minimum of the myocardium signal in magnitude TI-scout images. Whereas these method requires magnitude images, the embodiments described herein work on FIDDLE images which by their nature are PSIR images. Certain embodiments may also use magnitude images.

In an embodiment, the optimal TI may be adjusted over time. As the contrast agent (CA) concentration within the myocardium changes over time, the TI value determined at one time point may need to be adjusted for LGE acquisitions at later time points. An automated system including a deep learning based system may be used that outputs the time with darkest myocardium (TI) and linear regression model that adjusts the TI to output TI by considering the duration between the TI scout series and LGE imaging. A linear regression model may be used.

Figure 14:
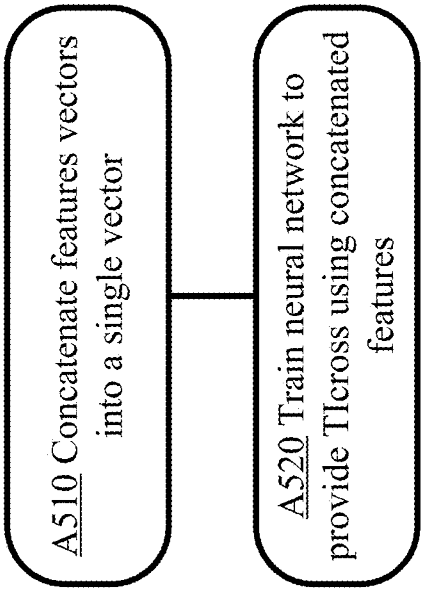
FIG. 14 depicts an example workflow for determining the crossing TI according to an embodiment.

FIG. 14 depicts an example workflow for determining the crossing TI, TIcross by training a neural network to regress the crossing TI. At act A510, for each FIDDLE TI-scout series, concatenate the feature vectors into a single vector to be used as the input to a neural network. To ensure that this concatenated feature vector has the same length for each patient's FIDDLE TI-scout image series, a value M representing the maximum expected number of feature vectors is defined. In N<M, the concatenated feature vector is padded with the values of the last feature vector in the series of vectors (feature vector #N). At act A520, using the feature vectors extracted for a series of FIDDLE TI-scouts, a neural network is trained to provide TIcross. The neural network is trained to solve a regression problem by selecting the inversion time where the myocardial and the blood pool's signals intersect, TIcross. In an example implementation the neural network may include three fully connected layers with 64, 32, and 1 neurons, with Rectified Linear Unit (ReLU) activation for the first two layers and linear activation for the last layer. Dropout may be used before the last layer to avoid overfitting. An L1 loss function is minimized using the Adam optimizer. Hyperparameter tuning can be run to select the best hyperparameters for a specific dataset. Typical hyperparameters obtained by proof-of-concept experiments are learning rate 0.05, batch size 4, and training epochs 300.

In another embodiment, a logarithmic fit is applied to determine the T1-recovery curves of blood and myocardium. Instead of training a neural network, an alternative solution to determining TIcross is to calculate the blood and normal myocardium recovery curves by standard curve fitting methods. A logarithmic, piecewise linear, or other target function may be used. A magnetization recovery curve in MRI is, to first order, an exponential recovery curve. Readout saturation is superimposed and affects the recovery curve as function of various parameters such as readout flip angle, echo spacing, and number of readout pulses per shot. Therefore, the measured curve is not purely an exponential recovery and a logarithmic or piecewise linear fitting will work. The crossing TI can be calculated as the TI where blood and myocardium have the same intensity, as indicated by the intersection of both curves.

At the respective TI value, TIcross, blood and normal myocardium have equal intensity in the FIDDLE image. This is a user-independent, objective assessment, from which a user-preferred, subjective optimal TI, TIopt, may be calculated. An analytical formula may be defined to calculate the optimal TI, TIopt, based on TIcross as input. This function can be customized to a user's preference to yield dark-blood or grey-blood FIDDLE images with a user-preferred contrast between blood pool and normal myocardium. For black blood FIDDLE, TIopt, is always shorter than TIcross. For example, in one embodiment TIopt could always be set 30 ms shorter than TIcross. In another embodiment, TIopt could be only slightly shorter than TIcross for small values of TIcross and be significantly shorter for bigger values of TIcross. One equation would be $TIopt=150/170\cdot(TIcross-170\text{ ms})+150\text{ ms}$. Using a TIopt>TIcross, the FIDDLE sequence can also create grey blood images. In that case, the system may set TIopt=TIcross+30 ms. Alternatively, the equation might be directly derived by applying a linear regression on a small (e.g., 30 samples) dataset of (TIcross, TIopt) pairs that have been annotated by a specific observer. In an alternative embodiment, a TI-detection network is trained directly on the optimal TI rather than on the crossing TI.

In another alternative, a fitting procedure may be used to model the normal myocardium and infarct recovery curves and calculate the TI where both curves intersect. Different types of fits may be used. One advantage of this solution compared to employing a neural network is that the recovery curves can be plotted, and the automatically calculated crossing TI can be confirmed by looking at the plot. Also, a-priori knowledge about the curve shape, which is to first order an exponential recovery, is intrinsically accounted for by using a curve model best fitting the true curve shape.

Embodiments described herein overcomes several challenges posed for an automatic TI selection of FIDDLE images, first regarding myocardium segmentation from FIDDLE images, and secondly regarding the subsequent TI prediction based on the segmentation mask. Embodiments use deep learning to train a neural network to perform myocardium segmentation on REF images associated with FIDDLE images. Since prior art segmentation only work on cine-type magnitude but not on REF images, embodiments apply a style transfer to cine images for generating synthetic REF images on which the neural network is then trained. This dramatically improves the segmentation performance on FIDDLE TI-scout images. A separate neural network is trained to find the intersection of the recovery curves of normal myocardium and blood pool. This separate neural network takes the FIDDLE TI-scout images and the myocardium and blood pool segmentation as input and produces the TI where the intersection occurs, TIcross, as output. The TIcross value may be used to select an optimal TI for a particular operator.

Referring back to FIG. 1, the system for determining an optimal TI includes a control unit 20 that includes one or more processors 22, a memory 24, and an interface 26. The control unit 20 may or may not be part of or co-located with the MR system 100. In an example, portions of the control unit 20 or functions thereof may be provided by a different machine, a server, or in the cloud. The control unit 20 may include one or more processors 22. The one or more processors 22 may include a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction, analysis, interpretation, and implementation for determining an optimal TI. The processor 22 may be a single device, a plurality of devices, or a network. For more than one device, parallel or sequential division of processing may be used. Different devices making up the processor may perform different functions, such as selecting a sequence by a first device, reconstructing by a second device, volume rendering by third device, and analysis by another device. In one embodiment, the processor 22 is a control processor or other processor of the MR system 100. Other processors of the MR system 100 or external to the MR system 100 may be used. The processor 22 is configured by software, firmware, and/or hardware to reconstruct. The instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The control unit 20 is configured to acquire, process, and analyze MR data and/or MR image data. The MR data and/or MR image data represents tissue, objects, blood, etc. of the patient. The medical data represents a one, two, or three-dimensional region of the patient. For example, the medical data represents an area or slice of the patient. Values are provided for each of multiple locations distributed in two or three dimensions. The medical data is acquired as a frame of data. The frame of data represents the scan region at a given time or period. The dataset may represent the area or volume over time, such as providing a 4D representation of the patient. The medical image or dataset is acquired by a scan of the patient. The acquisition occurs as part of the scan. Alternatively, the acquisition is from storage or memory, such as acquiring a previously created dataset from a PACS.

Figure 15:
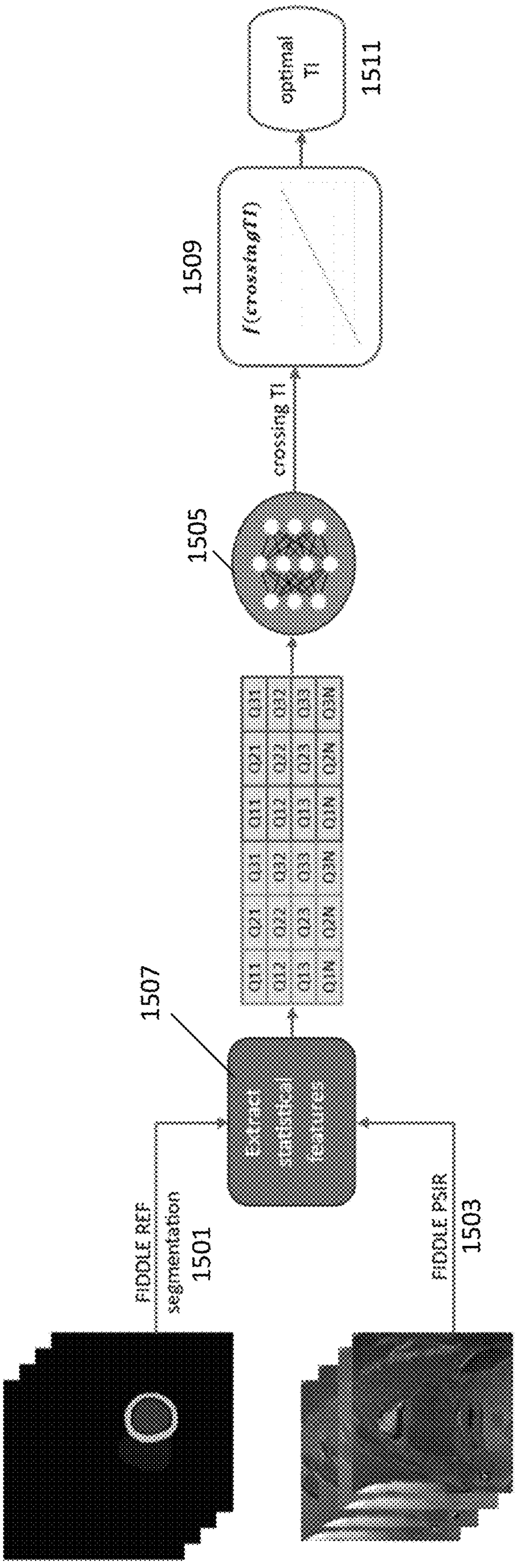
FIG. 15 depicts a workflow for automatically selecting the optimal TI for FIDDLE sequences according to an embodiment.

FIG. 15 describes a workflow for automatically selecting the optimal TI for FIDDLE sequences. FIDDLE REF segmentations 1501 are transferred to PSIR images 1503. Statistical measures are computed 1507 for the myocardium and blood pool signal in each FIDDLE TI-scout image. These features are passed through a neural network 1505 that regresses the crossing TI, TIcross 1509. An analytical formula is employed to obtain the optimal TI 1511, TIopt from TIcross.

In an embodiment, the control unit 20 is configured to assess the signal intensity of a tissue species in PSIR TI-scout images such as FIDDLE TI-scout images, rather than conventional magnitude images. Whereas isolating a tissue species by segmentation is needed to assess its signal intensity, this aspect may be independent of the quality and type of segmentation. Previous techniques only process magnitude TI-scout images. The generally accepted advantage of PSIR images is that a precise setting of TI is not necessary for obtaining good-quality PSIR LGE images. Rather, an approximate TI is sufficient since the contrast inversion possible in magnitude images with a too short TI does not occur in PSIR images. It is therefore counterintuitive to produce PSIR TI-scout images and it is non-obvious to devise a method that examines such PSIR images for finding an optimal TI.

In another embodiment, the control unit 20 is configured to assess two tissue species (normal myocardium and blood) in PSIR TI-scout images rather than a single one as previously done. In an embodiment, more than two species may be used, for example blood, normal myocardium, and scar. Previous methods to determine TI from a series of TI-scouts only track one tissue species, for example normal myocardium, since their only purpose is to find the TI that nulls normal myocardium. But for FIDDLE images specifically, which by definition are PSIR images, two tissue species (normal myocardium and blood) need to be assessed so that the crossing of their recovery curves can be found. Such an approach is not used for standard bright blood LGE images.

Furthermore, existing methods apply an end-to-end solution of determining the optimal TI directly from the input series of TI-scout images. This is not ideal since different technologists and operators have different preferences of an optimal image contrast so that the direct determination of TI by a neural network yields subjective results. To the contrary, embodiments break down the problem into smaller steps of a) determining the crossing TI, which is a user independent objective measure, and b) calculating the optimal TI from the crossing TI according to a user's subjective preference. This approach allows for a controlled subjectivity in determining the optimal TI for a desired FIDDLE contrast.

In addition, prior art neural networks are configured to pick one TI-scout image as having the optimal TI. These NNs classify TI-scouts into either "early" or "acceptable" images. This limits the prior art to only selecting one of the acquired TI values as optimal TI, but no TI value in-between. As the disclosed neural network is trained to solve a regression problem, it can also output intermediate values between acquired TI values, offering a finer TI resolution, and thereby providing more accurate results. For a TI-increment of 20 ms between consecutive TI-scout images, the mean absolute error between the annotated and automatically calculated crossing TI was 10.1±9.1 ms, with a maximum error of 55 ms. This is half the TI-increment and therefore twice as good as previously provided.

In another embodiment, the control unit 20 is configured to train a segmentation neural network in the context of a small number of PSIR reference training images that traditionally would be insufficient for an accurate training. Utilizing neural networks for segmenting a series of TI-scout images is one part of the above described processes. Existing segmentation networks that are trained on conventional, multi-cardiac phase magnitude breath-held TI-scouts do not properly segment free breathing, single-cardiac phase PSIR images. Training a neural network on PSIR images does not result in good segmentation quality either, because the contrast between blood and the myocardial wall is small for many images in the TI-scout series making it difficult to detect the endocardial border. Embodiments use the REF images for segmentation instead of PSIR images. Known TI-scout sequences and automatic TI-finding methods only produce and work on magnitude images. Previous method have used a segmentation network on phase reference (REF) images to obtain a myocardial and blood pool segmentation mask, and then applied these segmentation masks to the respective FIDDLE images, from which statistical features of myocardial and LV blood pool signal are extracted. To produce a neural network that works on REF images a segmentation neural network is pre-trained using either cine images or synthetic FIDDLE REF images created by a style transfer approach and using a cycle generative adversarial (cycleGAN) network. The segmentation neural network may then be finetuned on a small dataset of real FIDDLE REF images.

In an embodiment, as described in FIGS. 9 and 15, the control unit 20 pretrains a segmentation network on existing cine bSSFP short axis images with annotation, which is then finetuned on a few annotated FIDDLE REF images. In an example implementation, a Dense Unet segmentation network is pretrained on 90,000 cine bSSFP with manual annotation from approximately 5000 subjects in the UKBB public dataset. The architecture of the Dense Unet segmentation network may, for example, include five pooling layers with convolutions of 3×3. The loss to minimize can be chosen as Jaccard loss, while Adam may be used for the optimizer. In an example implementation, the input images are fed to the network in batches of 16; the weights may be updated using a learning rate of 0.001. The segmentation network is then finetuned using real FIDDLE REF images. In an example implementation the network was finetuned on real, i.e., acquired FIDDLE REF images from 77 subjects that had been manually annotated.

In another embodiment the style transfer and subsequent training includes training the style transfer network on paired cine and FIDDLE REF images, generating synthetic REF images from cine images, pretraining a Dense Unet, and finetuning the segmentation network using real FIDDLE REF images. The style transfer includes having the neural network learn the mapping between an input and output image, and vice-versa. In an example implementation the style transfer network is trained on paired FIDDLE REF and cine images of the same cardiac phase, both acquired under breath hold to minimize the effect of breathing motion. To generate a training dataset of aligned paired REF and cine images, a number of a breath hold REF images (e.g., three) may be sampled randomly and paired with the last a cine frames acquired at the same physical location, this selection ensuring that the images are in the same end-diastolic cardiac phase. Before providing these paired images as input to the model, they may be pre-processed, for example, resampling to 1×1 mm resolution, performing a clipping normalization by setting intensity pixel values higher than 95% quantile, e.g., higher than a threshold of 700, to the respective threshold, applying a Unity-based normalization to rescale pixel values in the range, and/or cropping the images to 150×150 mm around the image center, such that only left and right ventricle, and the myocardial wall remain visible.

After training the style transfer network, synthetic REF images are generated from cine images. In an example implementation, a number of more than 90 000 synthetic FIDDLE REF images were synthetically generated using the trained style transfer network from cine images from a number of approximately 5000 subjects where the myocardium had been previously manually annotated, that were in this case publicly available from the UKBB. The style transfer network was trained on 294 paired cardiac phase-matched cine-REF pairs from 102 subjects, for which balanced steady-state free precession cine images had been acquired in the same slice. The myocardium was manually segmented in the REF and cine images. The resulting synthetically generated FIDDLE REF images were paired with the original ground truth annotation of the cine images to train the segmentation network.

A Dense Unet segmentation network is then trained on the synthetic REF images. In an example implementation, the architecture may include five pooling layers with convolutions of 3×3. The loss to minimize can be chosen as Jaccard loss, while Adam is a common choice for the optimizer. For the example implementation, the input images were fed to the network in batches of 16; the weights were updated using a learning rate of 0.001 for 50 epochs. The segmentation network is then finetuned using real FIDDLE REF images, for example on real, i.e., acquired FIDDLE REF images from 77 subjects that had been manually annotated.

The MR data, image data, network/model data, weights etc. may be stored in the memory 24 of the control unit 20 alone with the instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps)

may differ depending upon the manner in which the present embodiments are programmed.

The output of the processes and methods may be output for further processing or displayed to an operator. The system 100 includes an operator interface 26, formed by an input and an output. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. The input may receive a scan protocol, imaging protocol, or scan parameters. An individual may select the input, such as manually or physically entering a value. Previously used values or parameters may be input from the interface. Default, institution, facility, or group set levels may be input, such as from memory to the interface.

The output is a display device but may be an interface. The images, for example, reconstructed from the imaging procedure are displayed. For example, an image of a region of the patient is displayed. A generated image of the reconstructed representation for a given patient is presented on a display of the operator interface 26. An analysis/interpretation may also be displayed on the display device. The control unit 20 may be configured to generate a report for the patient that is displayed on the display device. The display is a CRT, LCD, plasma, projector, printer, or other display device. The display is configured by loading an image to a display plane or buffer. The display is configured to display the reconstructed MR image of the region of the patient. The operator interface may include form a graphical user interface (GUI) enabling user interaction with the control unit 20 and enables user modification in substantially real time.

While the invention has been described above by reference to various embodiments, many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The following is a list of non-limiting illustrative embodiments disclosed herein:

Illustrative embodiment 1. A method for automatically calculating an optimal inversion time for flow independent dark-blood delayed enhancement (FIDDLE) acquisition, the method comprising: acquiring MR data of a patient, the MR data comprising a series of phase sensitive FIDDLE images, each having a different TI, and a series of phase reference images, each of which are associated with one phase sensitive FIDDLE image of the series of phase sensitive FIDDLE images; segmenting the series of phase sensitive FIDDLE images into a myocardial wall compartment and a blood pool compartment, using the series of phase reference images to derive segmentation contours for the phase sensitive FIDDLE images; calculating, from the myocardial wall compartment, a signal of normal myocardium in each of the phase sensitive FIDDLE images; calculating, from the blood pool compartment, a signal of blood in each of the phase sensitive FIDDLE images; grouping each pair of the normal myocardium signal and its respective TI into a signal-versus-TI function that represents a recovery curve of normal myocardium, and grouping each pair of the blood signal and its respective TI into a signal versus-TI function that represents a recovery curve of blood; determining a crossing TI from an intersection of the recovery curves and the respective TI; and calculating an optimal TI from the crossing TI.

Illustrative embodiment 2. The method according to illustrative embodiment 1, wherein segmenting comprises segmenting by a neural network configured for segmentation.

Illustrative embodiment 3. The method according to one of the preceding embodiments, wherein the neural network is trained on a series of synthetic phase reference images that were created from diastolic cine image frames by a style-transfer network.

Illustrative embodiment 4. The method according to illustrative embodiment 3, wherein the neural network is pretrained on the series of synthetic phase reference images and then additionally trained with a series of acquired phase reference images.

Illustrative embodiment 5. The method according to illustrative embodiment 3, wherein the style-transfer network comprises a CycleGAN network.

Illustrative embodiment 6. The method according to one of the preceding embodiments, wherein the signal of normal myocardium is computed as a lower quartile of all pixels contained in the myocardial wall compartment.

Illustrative embodiment 7. The method according to one of the preceding embodiments, wherein the signal of normal myocardium is computed as a median pixel intensity of all pixels contained in the myocardial wall compartment.

Illustrative embodiment 8. The method according to one of the preceding embodiments, wherein the signal of a blood pool is extracted as the mean or median pixel intensity of all pixels contained in the blood pool compartment.

Illustrative embodiment 9. The method according to one of the preceding embodiments, wherein the crossing TI is determined using a neural network trained to produce the crossing TI as output, wherein pairs of TI and at least one of the signal features of normal myocardium, lower quartile, upper quartile, median, and mean signal intensity, and pairs of TI and at least one of the signal features of blood, lower quartile, upper quartile, median, and mean signal intensity, are used as inputs to the neural network.

Illustrative embodiment 10. The method of according to one of the preceding embodiments, wherein the crossing TI is determined by fitting a first curve to all pairs of the signal of normal myocardium and TI, and fitting a second curve to all pairs of the signal of blood and TI, and determining the crossing TI where the first curve and second curve intersect.

Illustrative embodiment 11. The method of according to one of the preceding embodiments, wherein the optimal TI is calculated from the crossing TI as: optimal TI=150/170 times (Crossing TI−170 milliseconds)+150 milliseconds, wherein the optimal TI provides black blood PSIR images.

Illustrative embodiment 12. The method of according to one of the preceding embodiments, wherein the optimal TI is calculated from the crossing TI, as: optimal TI=crossing TI−30 milliseconds, wherein the optimal TI provides grey blood PSIR or magnitude images.

Illustrative embodiment 13. The method of according to one of the preceding embodiments, wherein a third compartment in addition to the myocardial wall compartment and the blood pool compartment is segmented and tracked as function of TI, wherein the optimal TI is determined based on the signals of all compartments.

Illustrative embodiment 14. The method of according to one of the preceding embodiments, wherein a relationship between the crossing TI and the optimal TI is directly derived by applying a linear regression on a set of (crossing TI, optimal TI) pairs that have been annotated by a specific observer.

Illustrative embodiment 15. A system for automatically calculating an optimal inversion time (TI) for flow independent dark-blood delayed enhancement (FIDDLE), the system comprising: a magnetic resonance scanner configured to acquire FIDDLE data, the FIDDLE data comprising a series of phase sensitive FIDDLE images, each having a different TI, and a series of phase reference images, each of which are associated with one phase sensitive FIDDLE image of the series of phase sensitive FIDDLE images; and a control unit configured to segment the series of phase sensitive FIDDLE images into a myocardial wall compartment and a blood pool compartment, using the series of phase reference images to derive the segmentation contours for the phase sensitive FIDDLE images, calculate, from the myocardial wall compartment, a signal of normal myocardium in each of the phase sensitive FIDDLE images, calculate, from the blood pool compartment, a signal of blood in each of the phase sensitive FIDDLE images, group each pair of the normal myocardium signal and its respective TI into a signal-versus-TI function that represents a recovery curve of normal myocardium, group each pair of the blood signal and its respective TI into a signal versus-TI function that represents a recovery curve of blood, determine a crossing TI from an intersection of the recovery curves and the respective TI, and determine the optimal TI from the crossing TI.

Illustrative embodiment 16. The system according to one of the preceding embodiments, wherein the control unit is configured to segment the series of phase sensitive FIDDLE images using a neural network configured for segmentation, wherein the neural network is pretrained on a series of synthetic phase reference images that were created from diastolic cine image frames by a style-transfer network and then additionally trained with a series of acquired phase reference images.

Illustrative embodiment 17. The system according to one of the preceding embodiments, wherein the control unit is configured to determine the crossing TI using a neural network trained to produce the crossing TI as output, wherein all pairs of the signal of normal myocardium and TI and all pairs of the signal of blood and TI are used as inputs to the neural network.

Illustrative embodiment 18. The system according to one of the preceding embodiments, wherein the control unit is configured to calculate the signal of normal myocardium as a lower quartile or median of all pixels contained in the myocardial wall compartment and/or wherein the control unit is configured to calculate the signal of a blood pool is extracted as the mean, or median pixel intensity of all pixels contained in the blood pool compartment.

Illustrative embodiment 19. The system according to one of the preceding embodiments, wherein the control unit is configured to determine the optimal TI: optimal TI=150/170 times (Crossing TI−170 milliseconds)+150 milliseconds, wherein the optimal TI provides black blood PSIR images or as: optimal TI=crossing TI−30 milliseconds, wherein the optimal TI provides grey blood PSIR or magnitude images.

Illustrative embodiment 20. A method for segmenting a series of phase sensitive FIDDLE images into a myocardial wall compartment and a blood pool compartment, the method comprising: generating, using a style transfer network, synthetic FIDDLE reference images; training, using the synthetic FIDDLE reference images, a segmentation neural network for segmenting image data into the myocardial wall compartment and the blood pool compartment; finetuning the segmentation neural network using a dataset of real FIDDLE REF images; and applying the trained segmentation neural network to the series of phase sensitive FIDDLE images to output the segmented myocardial wall compartment and blood pool compartment.

The invention claimed is:

1. A method for automatically calculating an optimal inversion time (TI) for flow independent dark-blood delayed enhancement (FIDDLE) acquisition, the method comprising:

acquiring MR data of a patient, the MR data comprising a series of phase sensitive FIDDLE images, each having a different TI, and a series of phase reference images, each of which are associated with one phase sensitive FIDDLE image of the series of phase sensitive FIDDLE images;

segmenting the series of phase sensitive FIDDLE images into a myocardial wall compartment and a blood pool compartment, using the series of phase reference images to derive segmentation contours for the phase sensitive FIDDLE images;

calculating, from the myocardial wall compartment, a signal of normal myocardium in each of the phase sensitive FIDDLE images;

calculating, from the blood pool compartment, a signal of blood in each of the phase sensitive FIDDLE images;

grouping each pair of the normal myocardium signal and its respective TI into a signal- versus-TI function that represents a recovery curve of normal myocardium, and grouping each pair of the blood signal and its respective TI into a signal versus-TI function that represents a recovery curve of blood;

determining a crossing TI from an intersection of the recovery curves and the respective TI; and calculating an optimal TI from the crossing TI.

2. The method of claim 1, wherein segmenting comprises segmenting by a neural network configured for segmentation.

3. The method of claim 2, wherein the neural network is trained on a series of synthetic phase reference images that were created from diastolic cine image frames by a style-transfer network.

4. The method of claim 3, wherein the neural network is pretrained on the series of synthetic phase reference images and then additionally trained with a series of acquired phase reference images.

5. The method of claim 3, wherein the style-transfer network comprises a CycleGAN network.

6. The method of claim 1, wherein the signal of normal myocardium is computed as a lower quartile of all pixels contained in the myocardial wall compartment.

7. The method of claim 1, wherein the signal of normal myocardium is computed as a median pixel intensity of all pixels contained in the myocardial wall compartment.

8. The method of claim 1, wherein the signal of a blood pool is extracted as the mean or median pixel intensity of all pixels contained in the blood pool compartment.

9. The method of claim 1, wherein the crossing TI is determined using a neural network trained to produce the crossing TI as output, wherein pairs of TI and at least one of the signal features of normal myocardium, lower quartile, upper quartile, median, and mean signal intensity, and pairs of TI and at least one of the signal features of blood, lower quartile, upper quartile, median, and mean signal intensity, are used as inputs to the neural network.

10. The method of claim 1, wherein the crossing TI is determined by fitting a first curve to all pairs of the signal of normal myocardium and TI, and fitting a second curve to all pairs of the signal of blood and TI, and determining the crossing TI where the first curve and second curve intersect.

11. The method of claim 1, wherein the optimal TI is calculated from the crossing TI as: optimal TI=150/170*(Crossing TI−170 milliseconds)+150 milliseconds, wherein the optimal TI provides black blood PSIR images.

12. The method of claim 1, wherein the optimal TI is calculated from the crossing TI, as: optimal TI=crossing TI+30 milliseconds, wherein the optimal TI provides grey blood PSIR or magnitude images.

13. The method of claim 1, wherein a third compartment in addition to the myocardial wall compartment and the blood pool compartment is segmented and tracked as function of TI, wherein the optimal TI is determined based on the signals of all compartments.

14. The method of claim 1, wherein a relationship between the crossing TI and the optimal TI is directly derived by applying a linear regression on a set of (crossing TI, optimal TI) pairs that have been annotated by a specific observer.

15. A system for automatically calculating an optimal inversion time (TI) for flow independent dark-blood delayed enhancement (FIDDLE), the system comprising: a magnetic resonance scanner configured to acquire FIDDLE data, the FIDDLE data comprising a series of phase sensitive FIDDLE images, each having a different TI, and a series of phase reference images, each of which are associated with one phase sensitive FIDDLE image of the series of phase sensitive FIDDLE images; and a control unit configured to segment the series of phase sensitive FIDDLE images into a myocardial wall compartment and a blood pool compartment, using the series of phase reference images to derive the segmentation contours for the phase sensitive FIDDLE images, calculate, from the myocardial wall compartment, a signal of normal myocardium in each of the phase sensitive FIDDLE images, calculate, from the blood pool compartment, a signal of blood in each of the phase sensitive FIDDLE images, group each pair of the normal myocardium signal and its respective TI into a signal-versus-TI function that represents a recovery curve of normal myocardium, group each pair of the blood signal and its respective TI into a signal versus-TI function that represents a recovery curve of blood, determine a crossing TI from an intersection of the recovery curves and the respective TI, and determine the optimal TI from the crossing TI.

16. The system of claim 15, wherein the control unit is configured to segment the series of phase sensitive FIDDLE images using a neural network configured for segmentation, wherein the neural network is pretrained on a series of synthetic phase reference images that were created from diastolic cine image frames by a style-transfer network and then additionally trained with a series of acquired phase reference images.

17. The system of claim 15, wherein the control unit is configured to determine the crossing TI using a neural network trained to produce the crossing TI as output, wherein all pairs of the signal of normal myocardium and TI and all pairs of the signal of blood and TI are used as inputs to the neural network.

18. The system of claim 15, wherein the control unit is configured to calculate the signal of normal myocardium as a lower quartile or median of all pixels contained in the myocardial wall compartment and/or wherein the control unit is configured to calculate the signal of a blood pool is extracted as the mean, or median pixel intensity of all pixels contained in the blood pool compartment.

19. The system of claim 15, wherein the control unit is configured to determine the optimal TI:

optimal TI=150/170*(Crossing TI−170 milliseconds)+150 milliseconds, wherein the optimal TI provides black blood PSIR images or as:

optimal TI=crossing TI+30 milliseconds, wherein the optimal TI provides grey blood PSIR or magnitude images.

* * * * *